United States Patent
Stokes et al.

[11] Patent Number: 6,041,643
[45] Date of Patent: Mar. 28, 2000

[54] GAS SENSOR WITH PROTECTIVE GATE, METHOD OF FORMING THE SENSOR, AND METHOD OF SENSING

[75] Inventors: Edward Brittain Stokes; John Yupeng Gui, both of Niskayuna, N.Y.

[73] Assignee: General Electric Company, Schenectady, N.Y.

[21] Appl. No.: 09/123,760

[22] Filed: Jul. 27, 1998

[51] Int. Cl.[7] .......................... G01N 7/00; G01N 27/04
[52] U.S. Cl. ............................ 73/31.06; 422/90
[58] Field of Search ................... 73/31.01, 31.06, 73/31.05; 422/90, 95, 96, 97, 82.06

[56] References Cited

U.S. PATENT DOCUMENTS

| | | |
|---|---|---|
| 3,844,160 | 10/1974 | Yamaoka . |
| 3,864,628 | 2/1975 | Klass et al. . |
| 4,112,737 | 9/1978 | Morgan . |
| 4,218,298 | 8/1980 | Shimada et al. . |
| 4,347,732 | 9/1982 | Leary . |
| 4,354,308 | 10/1982 | Shimada et al. . |
| 4,885,929 | 12/1989 | Kasahara et al. ............ 73/31.06 |
| 4,897,628 | 1/1990 | Ippommatsu et al. ............ 338/34 |
| 4,911,892 | 3/1990 | Grace et al. ............ 422/94 |
| 4,931,851 | 6/1990 | Sibbald et al. ............ 257/414 |
| 4,935,181 | 6/1990 | Theophilon et al. ............ 264/104 |
| 4,947,104 | 8/1990 | Pyke . |
| 4,953,387 | 9/1990 | Johnson et al. . |
| 5,147,523 | 9/1992 | Yagawara et al. ............ 204/424 |
| 5,250,170 | 10/1993 | Yagawara et al. ............ 204/431 |
| 5,384,470 | 1/1995 | Tachibana et al. ............ 257/77 |
| 5,417,821 | 5/1995 | Pyke . |
| 5,431,883 | 7/1995 | Barraud ............ 422/82.01 |

*Primary Examiner*—Hezron Williams
*Assistant Examiner*—Jay L. Politzer
*Attorney, Agent, or Firm*—Ernest G. Cusick; Noreen C. Johnson

[57] ABSTRACT

A gas sensor determines the presence of at least one designated gas in a gaseous environment. The gas sensor comprises a semiconductor substrate; a thin insulator layer disposed on the semiconductor substrate; a catalytic metallic gate disposed on the thin insulator layer; and a chemically modified layer disposed on the catalytic metal gate. The chemically modified layer comprises a material that protects the sensor from corrosive gases and interference from at least one foreign matter and water, alters at least one of surface chemical properties and surface physical properties of the sensor, and passes only the designated gas therethrough.

8 Claims, 1 Drawing Sheet

GAS SENSOR WITH PROTECTIVE GATE, METHOD OF FORMING THE SENSOR, AND METHOD OF SENSING

FIELD OF THE INVENTION

The invention is related to gas sensors. In particular, the invention is related to a gas sensor with a protective gate.

DISCUSSION OF RELATED ART

Gas and vapor sensors have many industrial applications. These applications include the detection of hazardous gas in the workplace for worker safety, enhanced control of the air-fuel mixture and feed in combustion of fuel, increased product yield and reduced waste in a product stream. These applications generally rely on individual sensors, which are installed to detect a single gas or vapor whose concentration may approach a harmful level. The examples of these gases include, but are not limited to, hydrogen sulfide, carbon monoxide, chlorine, ammonia, hydrogen, and methane.

Methods for industrial gas and vapor sensing have evolved basically along two technology paths. The first path involves use of complex analytical instruments, for example infrared spectroscopy, gas chromatography, and mass spectrometry. The development of microcontrollers and microcomputers has led to smaller versions of these analytical instruments. These instruments are very powerful, but they have significant disadvantages, such as being very maintenance intensive. Further, these instruments are sensitive to adverse, corrosive environments and must be located far from the gas or vapor source in a climate controlled enclosure. Thus, a gas (vapor) sample must be transported to the analyzer, as a result real time information is not available. Also, these instruments are expensive, and are thus not affordable candidates for real-time, in-situ applications.

The second technology path for industrial gas sensors developed with chemical sensor technologies. The applications of chemical sensors in chemical processes are well established, and these chemical sensors may be located in process streams to enhance process efficiency and yield, and to reduce waste. For example, water-concentration amount determination in a silicone process feed stream can be enhanced by using chemical sensors to sense water concentrations.

The ability of sensors to identify a target gas depends on several factors. These factors include the sensitivity of the sensor to other interfering gases and vapors, and a concentration of the target gas. The ability to resolve the target gas from other gases is called the selectivity. There are very few known sensors that are highly selective where a sensor has greater than about a tenfold difference in gas detection between sensing states and non-sensing states. Further, within these very few sensors there are even fewer that are relatively reliable to accurately detect individual gases. For example, an unreliable sensor does not provide correct indication of a gas amount when the concentration of an interferant is high. In practice, this limitation is avoided by using a sensor only where a high concentration of interferant is unlikely. This solution, however, limits the effectiveness and uses of a sensor.

Gas sensors have been used in detection of particular undesirable gases in oil-filled electrical transformers. Faults in an oil-filled transformer include arcing (electrical), corona discharge (electrical), low energy sparking (electrical), severe overloading (electrical), pump motor failure (electrical and thermal) and overheating (electrical and thermal) in an insulation system. Faults can generate undesirable gases, such as hydrogen ($H_2$), acetylene ($C_2H_2$), ethylene ($C_2H_4$), and carbon monoxide (CO). These fault conditions result in a transformer malfunctioning or indicate an impending malfunction, which, if not corrected, may lead to failure of the transformer. A statistical correlation exists between transformer malfunction and fault gases generated by the transformer. This correlation has use of gas to detect precursors of possible transformer malfunctioning. Accordingly, if an accurate detection of potentially dangerous gases in a transformer is achieved, possible malfunction and failure of the transformer can be addressed and often avoided.

One class of gas detection sensors normally comprise a semiconductor substrate, a thin insulator layer mounted, for example grown, on the semiconductor substrate, and a catalytic metallic gate mounted, for example deposited, on the thin insulator layer. Sensors of this nature are known. The sensor's level of sensitivity is different for each gas depending on the gate material. The gate material determines what designated gas will be detected, in other words, the gate material tunes the sensor for a designated gas. Accordingly, while an individual sensor may be useful to detect a single gas to which it is tuned, it will not be as useful to detect other gases. If the sensor is not appropriately tuned, the designated gas may not accurately detected, which of course is undesirable.

Further, known sensors do not provide protection of the sensor components from harmful environments. For example, corrosive gases are often present in a transformer, and adversely affect operation of a sensor. These corrosive gases in a transformer must be kept away from a sensor's catalytic gate in order for the sensor to operate accurately and properly. Also, these known sensors are not protected from water or particulate foreign matter interference, which are often found in transformers.

Some gas sensors have proposed the use of membranes, sieves and discontinuous layers of material to protect the sensor. However, these proposals are not seen to protect the sensor from corrosion, water and foreign particulate materials. The membranes, sieves and discontinuous layers are not secured to the sensor components so they do not adhere to and protect the sensor, especially the gate.

Therefore, it is desirable to provide a sensor that includes protection from corrosive environments, water, and foreign matter. It is also desirable to provide a sensor that can be designed to be tuned so as to selectively pass and detect a designated gas. Also, it is desirable to provide a system for monitoring concentrations of gases in various applications, for example in a manufacturing apparatus and failure mode monitoring of equipment process to power transformers.

SUMMARY OF THE INVENTION

Accordingly, the invention overcomes the above noted deficiencies in known gas sensors. A gas sensor that determines the presence of at least one designated gas in the ambient environment is disclosed in an embodiment of the invention. The gas sensor comprises a semiconductor substrate; a thin insulator layer mounted on the semiconductor substrate; a catalytic metallic gate mounted on the thin insulator layer; and a protective layer mounted on the catalytic metallic gate layer. The protective layer changes at least one of a surface chemical and physical property of the sensor. The protective layer is formed from a material that protects the sensor from corrosive environments and interference from at least one of particulates (minute separate particles that often result when oil degrades) and water. The protective layer enhances the sensitivity of the sensor to a designated gas, and permits the designated gas to pass through to the catalytic metallic gate. The catalytic metallic gate alters a designated gas, for example by heterolytic cleavage (decomposition into charged ions) of a C—H or H—H bond in the gas (herein "alters"). The resultant ionic, atomic hydrogen (H.) diffuses through the gate and varies electrical sensitivity of the sensor.

Also, in accordance with another embodiment of the invention, a method for sensing a designated gas in a gaseous state comprises providing a sensor, where the sensor includes a semiconductor substrate; an insulator layer disposed on the semiconductor substrate; a catalytic metallic gate layer disposed on the insulator layer; and a protective layer disposed on the catalytic metal gate. The protective layer changes at least one of the surface chemical and physical properties of the sensor. The protective layer is formed from a material that provides protection of foreign matter and water. The protective layer permits the designated gas to pass through to and interact with the catalytic metallic layer and reduces, and even prevents, passage of corrosive gases (chlorine and hydrogen sulfide), water, foreign matter (matter not intended to be associated with the sensor) and gases, other than the designated gas. The sensor is positioned in a gaseous environment that may comprise the designated gas to be sensed. The designated gas passes through the protective layer and is altered as it adsorbs onto the catalytic metal gate. The atomic hydrogen (H.) passes through the gate to the insulator layer, where it alters the altering electrical sensitivity of the sensor.

Further, another embodiment of the invention provides a method for forming a gas sensor for determining a designated gas. The method comprises providing an insulator layer on the semiconductor substrate; providing a catalytic metallic gate on the insulator layer; and providing a protective layer disposed on the catalytic metal gate. The protective layer changes at least one of a surface chemical and physical property of the sensor. The protective layer is formed from a material that provides protection from corrosive gases (chloride and hydrogen sulfide) and interference from at least one of foreign matter (matter not intended to be associated with the sensor) and water. The protective layer permits the designated gas to pass through to the catalytic metallic gate layer, where the designated gas is altered, for example on one of an atomic and molecular level. The protective layer reduces, and even prevents, passage of foreign matter, water and gases other than the protective designated gas, and alters the designated gas. The designated atomic hydrogen (H.) gas passes through the gate to the insulative layer, where the altered designated gas varies performance of the sensor by altering electrical sensitivity.

These and other aspects, advantages and salient features of the invention will become apparent from the following detailed description, which, when taken in conjunction with the annexed drawings, where like parts are designated by like reference characters throughout the drawings, disclose embodiments of the invention.

DESCRIPTION OF THE INVENTION

Figure 1:
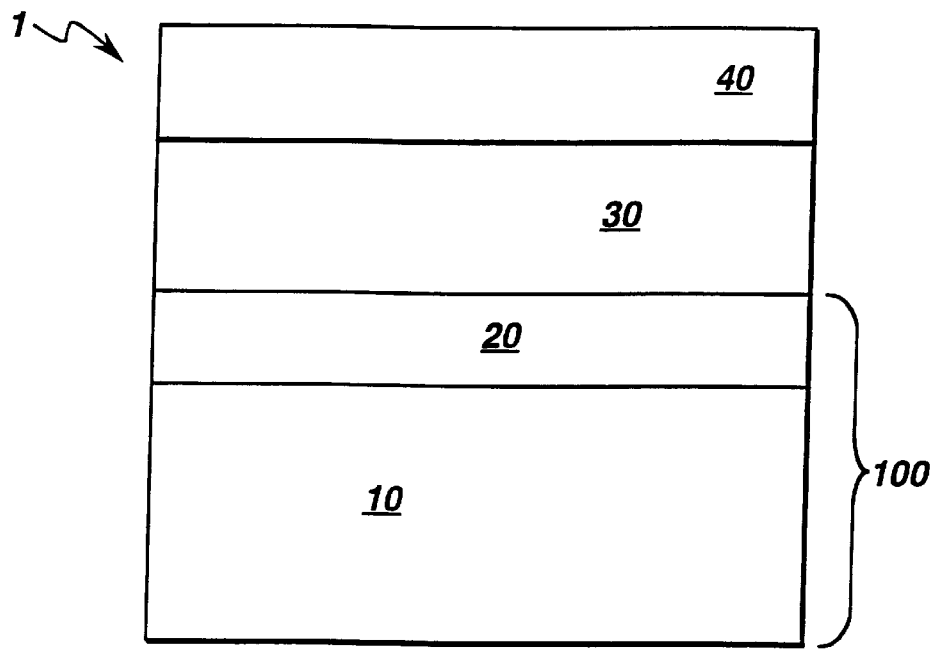
FIG. 1 is a cross-sectional view of a sensor with a protective gate.

Gas sensors, such as, but not limited to, a metal-insulator-semiconductor (MIS) diode gas sensor and a field effect transducer (FET) gas sensor, are known in the art. The sensors comprise a semiconductor substrate; a thin insulator layer mounted on the semiconductor substrate; and a catalytic metallic gate (gate) mounted on the thin insulator layer. These known sensors have been generally used for monitoring gas in clean, dry, noncorrosive environments.

A generalized operation of an MIS gas sensor will now be provided, using hydrogen gas as the detected gas. The sensor, its operation and the hydrogen gas are merely exemplary, and are not meant to limit the invention. Initially, hydrogen gas molecules ($H_2$) are adsorbed onto the metallic gate from the surrounding ambient environment. The adsorbed molecules are altered, such as by being catalytically dissociated from each other on one of a molecular or atomic level. For hydrogen gas ($H_2$), the molecules ($H_2$) are dissociated into individual hydrogen atoms (H.). Next, the atomic hydrogen (H.) diffuses through the metallic gate to a metal-oxide interface at the semiconductor substrate. This diffusion forms a dipole layer that modulates electrical conductance of the sensor and changes electrical conductivity of the substrate. Many individual gases containing hydrogen, such as, but not limited to, amines, mercaptans, hydrocarbons, and alcohols, can be detected in this manner by a sensor.

The level of sensitivity for each hydrogen-containing gas is different for each particular gate material. A sensor is tuned to a particular gas by virtue of the particular gate material. Known sensors provide adequate operation for a single hydrogen-containing gas in a clean, dry, noncorrosive environment. These known sensors, however, do not operate effectively if the environment is not clean and contains foreign matter (matter not intended to be associated with the sensor), such as particulates (minute separate particles that often result when oil degrades), or contains water vapor. Also, known sensors do not operate effectively if the sensor is placed in a corrosive gaseous (chlorine and hydrogen sulfide) environment, or if the sensor does not have a satisfactory tuned (sensitivity) level for the designated gas.

Accordingly, as embodied by the invention, a sensor comprises protective structure to protect the sensor in the presence of at least one of water vapor, foreign matter (matter not intended to be associated with the sensor), and corrosive gases (chlorine and hydrogen sulfide). The sensor comprises a gate material that provides a desirable sensitivity for a designated gas, such as a hydrogen-containing gas. The gate material will not be corroded in a corrosive gaseous environment, as is often found in electrical transformers, because of the protection afforded by the protective layer. Thus, the gas sensor 1 is positionable in corrosive environments and provides a real time data.

The invention will be described with a sensor in a transformer, which is merely an example of applications for the sensor. Other applications comprise gas detection in chemical process streams, enclosed potentially dangerous environments, and other places where detection of gases is desirable.

In a transformer, there are generally four gases that signify a fault or an impending fault. These faults and their underlying signifying gases are:

a.) Thermal-Oil-$C_2H_4$,
b.) Thermal-Cellulose-$CO_2$, CO
c.) Electrical Corona-$H_2$
d.) Electrical-Arcing-$H_2$, $C_2H_2$ Knowing this correlation, a possible fault type in a transformer can be evaluated by analysis of gases generated in a transformer.

As illustrated in FIG. 1, a gas sensor 1, in accordance with an embodiment of the invention, comprises a solid state sensor, for example a metal-insulator-semiconductor (MIS) sensor (also known as a metal-oxide-semiconductor (MOS) sensor). The MIS sensor is merely exemplary of sensors within the scope of the invention and will be used in the following description, but is not meant to limit the invention in any way.

The gas sensor 1 comprises semiconductor substrate 10, a layer of a thin insulator 20, and a catalytic metallic gate layer 30. A protective layer 40 is disposed over and mounted on the catalytic metallic gate 30. The protective layer 40 is disposed on the gate 30, for example, by deposition so the protective layer 40 adheres directly thereto in continuous and integral manner. The protective layer 40 provides a protective cover for the sensor 1 from at least one of a water vapor, corrosive gas and foreign matter, such as particulates. By virtue of the adherence of the protective layer 40 continuous and integral manner, the sensor 1 is protected and no contaminants may reach the gate 30.

In the modified gas sensor 1, the protective layer 40 changes surface chemical characteristics of the sensor 1. Alternatively, the protective layer 40 changes surface physical properties of the sensor 1. Further, as another alternative, the surface chemical and surface physical properties of the sensor 1 are changed by the protective layer 40.

The catalytic metallic gate layer 30 comprises a suitably thick layer of material of an appropriate corrosive-resistant gate material. For example, the material of the catalytic metallic gate layer 30 is comprises an appropriate metallic material, such as, but not limited to, at least one of: platinum, palladium, iridium, ruthenium, nickel, copper, rhodium, molybdenum, iron, cobalt, titanium, vanadium, tantalum, tungsten, chromium, manganese, gold, silver, aluminum, palladium:silver, tin, osmium, magnesium, zinc, alloys of these materials, and combinations of these materials. The catalytic metallic gate 30 comprises a layer that has a thickness in a range between about 5 nm to about 50 nm, preferably in a range between about 15 nm to about 30 nm, and even more preferably about 20 nm in thickness. The thickness of the catalytic metallic gate layer 30 depends on the intended use of the modified gate gas sensor 1.

The insulator layer 20 comprises an appropriate insulative material, such as silicon dioxide ($SiO_2$). However, any other appropriate material such as titanium oxide ($TiO_x$), silicone nitride and alumina ($Al_2O_3$) may be used for the insulator layer 20. The insulator layer 20 has a thickness generally in a range between about 1 nm to about 10 nm, and preferably about 5 nm in thickness. The thickness of the insulator layer 20 depends on the intended use of the modified gate gas sensor 1.

The semiconductor substrate 10 of the modified gate gas sensor 1 comprises an appropriate semiconductor material, such as, but not limited to, silicon, silicon dioxide, geranium, and other semiconductor materials. The insulator layer 20 and semiconductor substrate 10 define an insulator-on-semiconductor substrate system 100. In one embodiment of the invention, the insulator-on-semiconductor substrate system 100 comprises $SiO_2$ on silicon, however other insulator-on-semiconductor substrate systems 100 are within the scope of the invention. The exact combinations of materials of the catalytic metallic gate layer 30, the thin insulative layer 20, and the semiconductor substrate 10 can comprise any materials, as long as the protective layer 40 protects the sensor 1, as described herein.

The protective layer 40 changes (modifies) at least one of chemical properties and physical properties of the sensor 1. For example, the sensor 1 possesses modified chemical and physical properties provided by the protective layer 40, which prevents impurity adsorption. Further, the sensor 1 is chemical modified as the protective layer 40 provides a hydrophobic surface that reduces and possibly avoids water vapor interference.

The protective layer 40 improves the sensor's sensitivity by allowing only certain gases to pass through and interact with the catalytic metal gate layer 30. Amounts of other gases, as well as foreign matter, that pass through the protective layer 40 are reduced, and even prevented, from passing through. Accordingly, the sensor 1 possesses altered physical properties. Further, the surface chemical properties of the sensor 1 are altered, as the protective layer 40 changes materials that interact with the sensor 1.

The protective layer 40 comprises at least one layer, where the at least one layer comprises a single atom thick layer, for example, a layer formed by placement a single atom thick layer on the gate layer 30, such as deposition of a layer of iodine atoms. Alternatively, the protective layer 40 comprises a layer formed deposition of a multiple atoms thick layer, where the layer is at least two atoms in thickness. Also, as another alternative, the protective layer 40 comprises a molecular layer, for example, a layer formed by deposition of a layer of small molecules, such as a layer of a relatively complex organic molecules such as polytetrafluoroethylene. Further as another alternative, the protective layer 40 comprises a polymeric layer, for example, a layer formed by deposition of a thin film polymeric material, such as a thin film of hydrophobic polytetrafluoroethylene. The material and depth of the protective layer 40 is selected for sensitivity and performance with respect to the designated gas to be detected.

The protective layer 40 is disposed on the metallic gate layer 30 during manufacture of the sensor 1, for example by deposition, screening, coating, and other appropriate manufacturing techniques. Alternatively, the protective layer 40 is disposed on an existing sensor, after the sensor has been finally manufactured, to modify the existing sensor. With a modification of an existing sensor, a plurality of sensors can be manufactured, providing separate gate materials for tuning. The existing sensors possess essentially identical structures and characteristics, and the protective layer 40, which is disposed on the existing sensor after its manufacture, provides the sensor with its tuning for passage of the designated gas. Thus, depending on the protective layer 40, an array of modified gas sensors can be formed to provide, for example, real time responses to designated gases.

Figure 2:
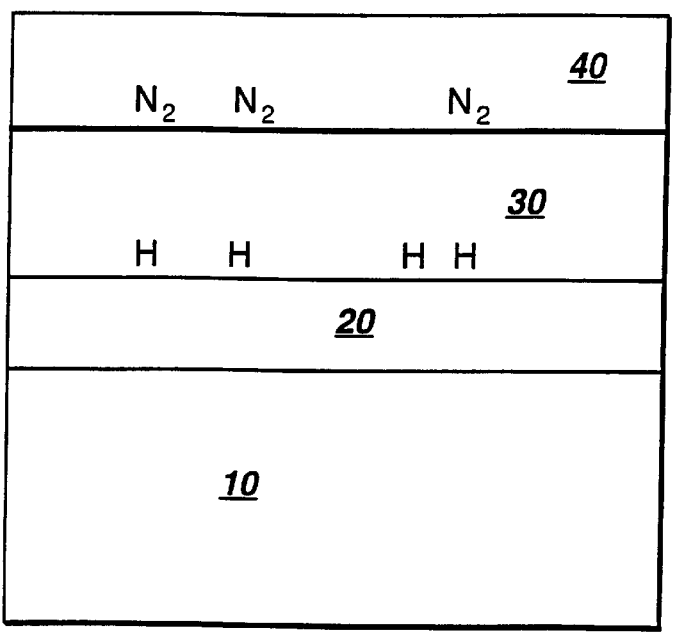
FIG. 2 is a cross-sectional view of a sensor schematically illustrating one example of the operation of the sensor.

An exemplary operation of a gas sensor 1 with a protective layer 40 will now be discussed, with reference to FIG. 2. The following operation uses a sensor tuned to have a sensitivity to hydrogen, however this is not meant limit the invention in any way. A sensor, as embodied by the invention, comprises materials so the sensor is tuned and detects a designated gas, for example real time data of the gas.

In operation, a modified gate gas sensor 1 is placed in a location with an ambient environment 50 containing the designated gas to be sensed, for example hydrogen. The ambient environment 50 comprises any number of gases and foreign matter, such as particulates. The protective layer 40 permits passage of the hydrogen molecules ($H_2$) only. Other gases and foreign matter do not pass through the protective layer 40. The protective layer 40 protects the sensor 1 from damage from corrosive gases, water, and foreign matter, such as particulates, by not allowing these to pass therethrough.

Once the molecular hydrogen $H_2$ passes through the protective layer 40, it interacts with the catalytic metallic gate 30. There the hydrogen molecules are then heterolytically cleavaged (altered) into hydrogen atoms (H.). The atomic hydrogen (H.) then passes through the thin insulator layer 20, where the electrical conductance sensitivity of the semiconductor substrate 10 of the gas sensor 1 is altered (as described above). Accordingly, the sensor 1 selectively detects the designated gas in the ambient atmosphere 50. An associated diagnostic system (not illustrated), which is attached to sensor 1 determines the designated gas and its amount as a result of the altered electrical conductivity.

While various embodiments are described herein, it will be appreciated from the specification that various combinations of elements, variations or improvements therein may be made by those skilled in the art, and are within the scope of the invention.

We claim:

1. A sensor that is designed for detection of a gas, the sensor comprising:
    a semiconductor substrate;
    an insulator layer disposed on the semiconductor substrate;
    a catalytic metallic gate layer disposed on the insulator layer; and
    a protective layer disposed on the catalytic metal gate, the protective layer comprising a material that provides one of protection from a corrosive gas and interference from at least one of foreign matter and water; the protective layer comprising a single atomic monolayer of iodine atoms;
    wherein the protective layer permits the designated gas to interact with the catalytic metallic gate layer, and reduces passage of at least one of: gases, other than the designated gas; water; and foreign matter.

2. A sensor according to claim 1, the catalytic metallic gate layer comprises a material selected from:
    platinum, palladium, iridium, ruthenium, nickel, copper, rhodium, molybdenum, iron, cobalt, titanium, vanadium, tantalum, tungsten, chromium, manganese, gold, silver, aluminum, tin, osmium, magnesium, zinc, alloys of the materials, or combinations of the materials.

3. A sensor according to claim 1, wherein the catalytic metal gate layer comprises a gate formed from one of platinum, palladium and palladium:silver.

4. A sensor according to claim 1, wherein the protective layer is electrically inert, non-conductive, and electrically insulating.

5. A method for sensing a designated gas in a gaseous environment, the method comprising:
    providing a sensor, the sensor comprising:
        a semiconductor substrate;
        an insulator layer disposed on the semiconductor substrate;
        a catalytic metallic gate layer disposed on the insulator layer; and
        a protective layer disposed on the catalytic metal gate, the protective layer comprising from a material that provides protection of the sensor from a corrosive gas and interference from at least one of foreign matter and water; the protective layer permits the designated gas to pass through to the catalytic metallic gate layer, and prevents passage of at least one of gases other than the designated gas, water and foreign matter; and the protective layer comprising a single atomic monolayer of iodine atoms;
    exposing the sensor to a gaseous environment that may comprise the designated gas to be sensed;
    allowing the gaseous environment to pass through and interact with the catalytic metallic gate layer, where the protective layer reduces amounts of water, foreign matter, and gases, other than the designated gas from passing through it;
    altering the designated gas as it contacts the catalytic metal gate, the altering comprising at least one of atomically and molecularly altering chemical structure of the designated gas;
    allowing the altered designated gas to pass to the insulator layer; and
    altering the sensitivity of the sensor.

6. A method according to claim 5, wherein the altering further comprises:
    dissociating molecular gases into at least one of atomic and molecular constituents.

7. A method according to claim 5, further comprising selecting the catalytic metallic gate from:
    platinum, palladium, iridium, ruthenium, nickel, copper, rhodium, molybdenum, iron, cobalt, titanium, vanadium, tantalum, tungsten, chromium, manganese, gold, silver, aluminum, tin, osmium, magnesium, zinc, alloys of the materials, or combinations of the materials.

8. A method according to claim 5, wherein the protective layer is electrically inert, non-conductive, and electrically insulating.

\* \* \* \* \*